(12) United States Patent
Samuelsson

(10) Patent No.: US 7,600,516 B2
(45) Date of Patent: Oct. 13, 2009

(54) DEVICE FOR PREVENTING TRANSMISSION OF BODILY FLUIDS DURING SEXUAL RELATIONS

(75) Inventor: Bo E. Samuelsson, Stockholm (SE)

(73) Assignee: JS Sakerhetssystem AB, Stockholm (SE)

( * ) Notice: Subject to any disclaimer, the term of this patent is extended or adjusted under 35 U.S.C. 154(b) by 142 days.

(21) Appl. No.: 10/529,211

(22) PCT Filed: Nov. 6, 2003

(86) PCT No.: PCT/SE03/01711
§ 371 (c)(1),
(2), (4) Date: Jan. 17, 2006

(87) PCT Pub. No.: WO2004/043309
PCT Pub. Date: May 27, 2004

(65) Prior Publication Data
US 2006/0137692 A1   Jun. 29, 2006

(30) Foreign Application Priority Data
Nov. 13, 2002   (SE) .................................. 0203344

(51) Int. Cl.
*A61F 6/04* (2006.01)

(52) U.S. Cl. ...................................... 128/844; 128/918

(58) Field of Classification Search ................. 128/844, 128/842, 918; 604/346, 355, 349, 347
See application file for complete search history.

(56) References Cited

U.S. PATENT DOCUMENTS

| 3,951,141 A | 4/1976 | Kopelowicz |
| 5,458,114 A * | 10/1995 | Herr ........................... 128/842 |
| 6,298,853 B1 | 10/2001 | Blake |

OTHER PUBLICATIONS

International Search Report.
International Preliminary Examination Report on Patentability.

* cited by examiner

*Primary Examiner*—Patricia Bianco
*Assistant Examiner*—Camtu T Nguyen
(74) *Attorney, Agent, or Firm*—Harness, Dickey & Pierce, P.L.C.

(57) ABSTRACT

A device for preventing transmission of bodily fluids during sexual relations from a first person to a second person, wherein the second person is male, may include a first part and a second part. The device may be formed of elastic material. The first part may have an inner side. At least a portion of the inner side may be coated with glue to fix the device to the sexual organ of the second person. The second part may include a material or membrane that is designed to repute upon ejaculation of the second person. The second part further may include a stiffer portion configured to be at least partially disposed in the urethra of the sexual organ of the second person.

8 Claims, 1 Drawing Sheet

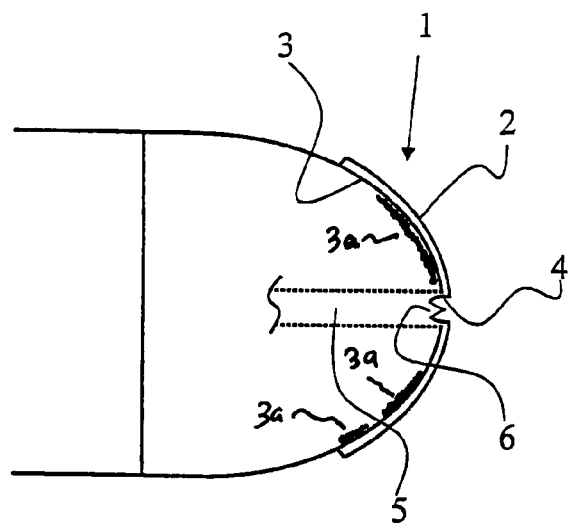
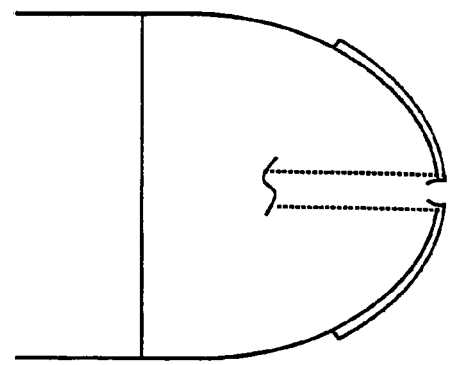
Fig 1a          Fig 1b
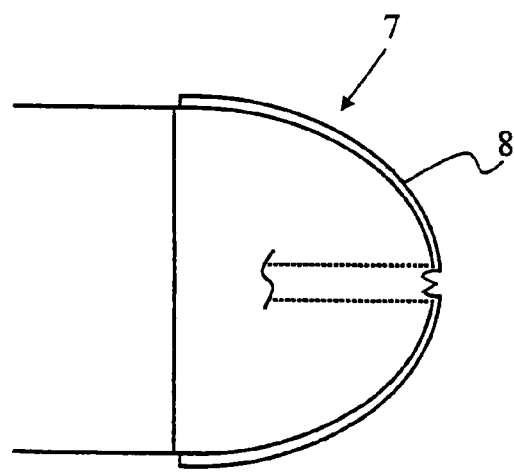
Fig 2

DEVICE FOR PREVENTING TRANSMISSION OF BODILY FLUIDS DURING SEXUAL RELATIONS

TECHNICAL FIELD

The present invention relates to a device for preventing or drastically reducing the risk of transmission of infection during sexual relations.

BACKGROUND OF THE INVENTION

A commonly discussed health problem nowadays is that of sexually transmitted diseases. This problem is not only the subject of general anxiety but is also discussed within various public bodies, for example the WHO (World Health Organization), as one of the really major, international health problems with which the international community is faced within the immediate future. Enormous sums are being spent on finding medicines which are effective against, for example, HIV and AIDS. But other diseases also, even if not with as drastic a progression, cost society billions of Kronor each year in healthcare and medicine costs. These diseases include, to quote just a few examples, condyloma, gonorrhea and syphilis. The diseases are both of the viral type and of the bacterial type. In terms of bacterial diseases, it can also be stated that an ever increasing number of resistant and multi-resistant strains of bacteria are developing, creating major problems for healthcare.

An increased use of condoms in intercourse has been regarded as a way of preventing increased spread of sexually transmitted diseases. Various voluntary, governmental and intergovernmental organizations are working very hard on informing and disseminating knowledge on how sexually transmitted diseases are spread and how spreading can be prevented by the use of a condom.

Early condoms consisted of parts of the intestine of suitable animals, which could be washed and reused. The main object of older condoms was to prevent conception. A modern condom can be described as a rubber sheath which is slipped, or rolled, onto the man's erect sexual organ. As a result of the rubber being stretched when applied to the man's sexual organ, a force is generated which presses the condom against the sexual organ. Through interaction with friction forces, the condom thus remains relatively securely fixed on the sexual organ during intercourse. When the man's sexual organ, after intercourse, reduces in size, the condom is easy to remove.

For modern condoms, too, the main object is, of course, to prevent conception. However, the condom has become increasingly passed over as a contraceptive now that other types have come into being, for example the pill, mini-pill and day-after pill. Its capacity to prevent transmission of infection has thus gained increasingly in importance. The transmission of infection is essentially averted by preventing an exchange of body fluids between the man and woman during intercourse, this by enclosing the man's sexual organ in a rubber sheath.

However, the use of a condom suffers from a number of problems. To prevent the condom from rupturing during intercourse, owing to friction forces between for example, condom and walls of the vagina, the condom wall must have a certain thickness. Moreover, the condom must be stretched over essentially the whole of the man's sexual organ if it is not to risk slipping off during intercourse. This impairs the sexual experience for the man and is a feature which causes many people to stop using a condom, with an increased risk of infection by sexually transmitted diseases.

As a result of the condom being stretched over the whole of the sexual organ, it is also occasionally subjected to relatively high friction forces at the moment of penetration, for example, or during intercourse, when the side of the man's sexual organ rubs against the walls of the vagina. If the condom has not then been made sufficiently strong, it is at risk of rupturing, which can happen essentially like a balloon owing to the rubber having been stretched and the condom thus losing its preventive and protective capacity.

Another drawback with condoms according to the prior art is that if the man lingers in the woman's vagina after intercourse, or if the man's sexual organ is not fully erect throughout intercourse, the condom is at risk of sliding off when the tension forces in the rubber cease as a result of the reduced size of the sexual organ. This increases, of course, the risks of exchange of body fluids and hence conception or spreading of sexually transmitted diseases.

Also of note is the fact that if infection can be prevented from occurring in the one direction, for example it is difficult or impossible for a woman to infect a man, then the spread of sexual diseases will substantially decrease. This can be especially important in situations in which men come into contact with women who regularly have sexual relations with a large number of men, for example in a brothel operation. Here it is especially important for the man to protect himself against sexually transmitted diseases.

SUMMARY OF THE INVENTION

The present invention offers a new type of device that tackles or severely reduces the aforementioned problems.

With a device according to claim 1, a device is provided which is free from the drawbacks which have been described above. The fact that a glue is used to fix the device to the penis prevents the device from sliding off and the fact that the device is contrived to burst upon ejaculation obviates the need for a sperm-collecting pouch.

According to a first preferred embodiment, the device according to the invention is fixed only to a front part of a glans. The sexual experience is hence minimally impaired, whilst a reasonable level of protection is maintained for sexually transmitted diseases from the woman to the man.

According to a second preferred embodiment, the device is fixed to essentially the whole of the glans, in which case a somewhat better protective effect is obtained.

According to a further embodiment, the glue is designed to fix to human skin and to maintain its adhesiveness when the glue is exposed to the fluids which occur naturally in humans and especially in the vagina and on the penis during intercourse. These fluids comprise various types of secretions and seminal fluid, but also blood and saliva. The glue is further contrived to lose its adhesiveness, or be dissolved, when a liquid or substance is applied which does not occur naturally in the human body. Such a liquid might be especially made for the purpose, for example a solvent of the dimethyl ketone type, or a liquid which is normally easily available, for example ethanol.

According to yet another embodiment, the glue is contrived to lose its adhesiveness after a period. This can be especially expedient if there is no liquid available for dissolving the glue.

BRIEF DESCRIPTION OF FIGURES

FIGS. 1*a* and 1*b* show in diagrammatic representation a device for preventing transmission of bodily fluids during sexual relations according to a first embodiment of the invention; FIG. 2 shows in diagrammatic representation a device for preventing transmission of bodily fluids during sexual relations according to a second embodiment of the invention.

PREFERRED EMBODIMENTS

FIG. 1a shows in diagrammatic representation a device 1 according to one embodiment of the invention. The device may be formed of an elastic material. A first part 2 has an inner side 3 which is coated with a glue 3a. The glue 3a is of such a type that it fixes on human skin, cf. plaster, and is not dissolved by body fluids, such as blood, urine, seminal fluid, etc. Inner side 3 may be formed as a substantially flat or weakly bending disk as shown, for example, in FIG. 1a. A second part 4 comprises a stiffer material contrived to be introduced into the man's urethra 5. The second part 4 has a somewhat rounded shape for easier introduction into the urethra. At the end of the second part 4 there is a fragile membrane 6. The membrane 6 is designed to burst upon ejaculation, whereupon the seminal fluid is freely able to leave the urethra 5, as is shown in FIG. 1b. The introduction of the thin membrane 6 into the urethra means that it is protected during intercourse and only bursts upon ejaculation. Since the second part 4 extends at least a little into the urethra 5, the outer parts of the urethra 5 and the top of the glans are also protected after the membrane 6 has burst. No further penetration of body fluids into the urethra 5 will occur.

Second part 4 may include a first, stiffer portion, provided to be at least partially situated in the man's spermatic duct, and a second, more brittle portion provided to burst upon ejaculation. When the second, more brittle portion bursts upon ejaculation, the man's seminal fluid may flow freely through device 1.

At the prospect of intercourse, the device 1 is placed on the glans, whereupon the glue disposed on the inner side 3 fixes to the skin of the glans and prevents the device 1 from falling off. The device 1 can be fixed both in the non-erect and in the erect state.

According to one aspect of the invention, a protective film is seated on the inner side 3 to cover the glue. The protective film is removed immediately prior to the device 1 being applied to the penis. According to a second aspect of the invention, the inner side 3 is coated with a first component of a two-component glue. By itself, the first component is non-adhesive. In this case, too, a protective film can be expedient in order to protect said first component from being inadvertently removed from the inner side 3. A second component of said two-component glue is contrived to be applied to the man's glans. The two components are contrived to create a strong adhesion upon contact with each other, in known fashion. For example, the inner side 3, coated with the first component, may be applied to the man's glans, coated with the second component. In this way, the device 1 is fixed to the man's glans.

As discussed above, the glue may be of the two-component type, with a first component and a second component. Inner side 3 may be coated with the first component that is non-adhesive. A part of the man's sexual organ may be coated with the second component. Application of inner side 3, coated with the first component, to the part of the man's sexual organ, coated with the second component, may fix the device to the man's sexual organ.

The glue is dissolved by dipping the penis in or coating it with a solvent, for example dimethyl ketone, methanol or ethanol. Ethanol is perhaps most suitable in this case, since it is generally close to hand and is often sold in shops which stay open all night.

According to another aspect, the glue can also be contrived to be adhesive only for a limited period, in which case the device 1 thus, after a time, falls off by itself. This time must, of course, be substantially longer than normal intercourse.

FIG. 2 shows a device 7 according to a second embodiment of the invention. According to this embodiment, a first part 8 is larger and is contrived to cover essentially the whole of the glans of the man's sexual organ. A larger surface is herein obtained for fixing of the device 7.

The device 1 or device 7 may prevent transmission of body fluids between two persons, at least one of whom is male, during sexual relations. The device 1 or device 7 is formed of elastic material and has an inner side, at least a part of which is coated with glue provided to fix the device to the man's sexual organ. At least a second part of the device 1 or device 7 includes a material that is provided to rupture upon ejaculation.

The invention claimed is:

1. A device for preventing transmission of bodily fluids during sexual relations from a first person to a second person, wherein the second person is male, the device comprising:
   a first part; and
   a second part;
   wherein the device is formed of elastic material,
   wherein the first part has an inner side,
   wherein at least a portion of the inner side is coated with glue to fix the device to the sexual organ of the second person,
   wherein the second part includes a material that is designed to rupture upon ejaculation of the second person, and
   wherein the second part further includes a stiffer portion configured to be at least partially disposed in the urethra of the sexual organ of the second person.

2. The device of claim 1, wherein the material that is designed to rupture upon ejaculation of the second person is a membrane.

3. The device of claim 1, wherein the inner side is formed as a substantially flat or weakly bending disk,
   wherein a middle of the first part merges into the second part, and
   wherein the first part is designed to be fixed over the mouth of the urethra of the sexual organ of the second person.

4. The device of claim 1, wherein an end of the first part merges into the second part, and
   wherein the first part is designed to be fixed over the mouth of the urethra of the sexual organ of the second person.

5. The device of claim 1, wherein the glue retains fastening capacity under action of normal bodily fluids, and
   wherein the glue is dissolved upon application of a liquid that does not normally occur naturally in humans.

6. The device of claim 5, wherein the liquid is an organic solvent.

7. The device of claim 5, wherein the liquid is ethanol.

8. The device of claim 1, wherein the glue is of a two-component type,
   wherein the inner side is coated with a first component that is non-adhesive,
   wherein a second component is provided to be coated on a part of the sexual organ of the second person, and
   wherein application of the inner side, coated with the first component, to the part of the sexual organ of the second person, coated with the second component, fixes the device to the sexual organ of the second person.

* * * * *